United States Patent
Ishii et al.

(10) Patent No.: US 7,930,925 B2
(45) Date of Patent: Apr. 26, 2011

(54) METHOD OF MEASURING HYDROGEN CONCENTRATION IN MEMBER AND DEVICE OF MEASURING HYDROGEN CONCENTRATION

(75) Inventors: Yoshiaki Ishii, Yokohama (JP); Akihiro Miyazaki, Futaba-Gun (JP); Masafumi Nakatsuka, Mito (JP); Shinji Ishimoto, Hitachinaka (JP)

(73) Assignee: Global Nuclear Fuel-Japan Co., Ltd., Yokosuka-Shi (JP)

( * ) Notice: Subject to any disclaimer, the term of this patent is extended or adjusted under 35 U.S.C. 154(b) by 543 days.

(21) Appl. No.: 11/908,863

(22) PCT Filed: Mar. 16, 2006

(86) PCT No.: PCT/JP2006/305248
§ 371 (c)(1),
(2), (4) Date: May 1, 2008

(87) PCT Pub. No.: WO2006/098404
PCT Pub. Date: Sep. 21, 2006

(65) Prior Publication Data
US 2009/0056415 A1    Mar. 5, 2009

(30) Foreign Application Priority Data
Mar. 16, 2005  (JP) .............. 2005-075702

(51) Int. Cl.
*G01N 23/00*    (2006.01)
(52) U.S. Cl. ................................. 73/24.02
(58) Field of Classification Search .......... 73/24.02
See application file for complete search history.

(56) References Cited

FOREIGN PATENT DOCUMENTS
JP    5 87714    4/1993
(Continued)

OTHER PUBLICATIONS

Nakatsuka, M. et al.,"Development of Non-destructive Hydrogen Measurement Method for Fuel Assembly Component Materials", Atomic Energy Society of Japan, vol. 3, p. 588, 2005.
(Continued)

*Primary Examiner* — Hezron Williams
*Assistant Examiner* — Rodney T Frank
(74) *Attorney, Agent, or Firm* — Oblon, Spivak, McClelland, Maier & Neustadt, L.L.P.

(57) ABSTRACT

An art of hydrogen concentration measurement in which the hydrogen concentration of any given location of an object to be measured can be nondestructively obtained is provided.
The steps comprises: placing an electromagnetic ultrasonic sensor 2 in the proximity of, or on, the surface of an object to be measured 8, said electromagnetic ultrasonic sensor 2 generating a magnetic field in which the magnetic flux density changes at high frequency on the wall body of the object to be measured 8 and receiving a longitudinal ultrasonic wave whose vibration is deflecting in the direction parallel to the thickness direction and a transverse ultrasonic wave whose vibration is deflecting in the direction at an angle of substantially 90° with respect to said longitudinal direction; allowing the electromagnetic ultrasonic sensor 2 to generate a changing magnetic field so that the longitudinal ultrasonic wave and the transverse ultrasonic wave form a resonant state and receive the longitudinal ultrasonic wave and the transverse ultrasonic wave generated in the object to be measured 8; detecting the resonance frequencies of the longitudinal ultrasonic wave and the transverse ultrasonic wave; calculating a predetermined resonance property index using said resonance frequencies of the longitudinal ultrasonic wave and the transverse ultrasonic wave; and calculating the hydrogen concentration of the object to be measured 8 with reference to a reference material database 7 which stores the relation between the hydrogen concentration of a member with the same member specifications as those of said object to be measured and the resonance property index.

4 Claims, 5 Drawing Sheets

FOREIGN PATENT DOCUMENTS

| | | |
|---|---|---|
| JP | 5 87780 | 4/1993 |
| JP | 07-286995 | 10/1995 |
| JP | 9 89542 | 4/1997 |
| JP | 2772481 | 4/1998 |
| JP | 2000-146923 | 5/2000 |
| JP | 2002 181795 | 6/2002 |
| JP | 2004-101281 | 4/2004 |

OTHER PUBLICATIONS

De. P. K. et al.,"Assessment of Hydrogen Levels in Zircaloy-2 by Non-destructive Testing", Journal of Nuclear Materials, vol. 252, pp. 43-54, 1998.

Japanese Office Action (with English translation) issued on Feb. 8, 2011, in Japanese Patent Application No. 2005-075702 (5 pages).

METHOD OF MEASURING HYDROGEN CONCENTRATION IN MEMBER AND DEVICE OF MEASURING HYDROGEN CONCENTRATION

FIELD OF THE INVENTION

The present invention involves a method and an instrument for measuring hydrogen concentration in a metal material.

Particularly the present invention relates to a method and an instrument to enable nondestructive measurement of hydrogen concentration in a metal material using the resonance property of elastic waves (ultrasonic waves) electromagnetically generated directly in the material.

BACKGROUND ART

A generally and widely employed destructive measurement method for measuring hydrogen concentration in a metal material is, as shown in ASTM E1447-92, a method wherein: an object to be measured is cut into fragments of 1 gram or less, dried after washing, transferred into a heat-resisting crucible, melted at the melting point of the sample or a lower temperature with a flux composed of pure metal; hydrogen is extracted together with other gases from the object to be measured; the amount of the hydrogen gas is determined by the change in the thermal conductivity of the extracted gasses collected in a fixed container; and the hydrogen concentration is calculated.

However, the implementation of the above method is often practically difficult because the object to be measured is subject to destruction. Particularly, if the object is a radioactive metal, the problem of excessively large cost and facility required for disposal of the contaminants arises.

For these reasons, a method for nondestructively measuring hydrogen concentration in a metal material is highly demanded.

As a nondestructive method, firstly there is a method making use of electromagnetic properties.

In this method, an eddy-current sensor probe including a coil is placed on the surface of an object to be measured, and the above coil is excited by applying an alternating current. This allows eddy current generation in the electrically conducting object to be measured by electromagnetic induction. It is known that electromagnetic characteristics of a metal material, including the electric conductivity, magnetic permeability, etc. of the metal, change, though only slightly, depending on the magnitude of the ratio of the hydride precipitates in the metal to be analyzed.

Making use of this, the hydrogen concentration in an object to be analyzed can be detected by measuring the electric conductivity, magnetic permeability, etc. of the object to be measured. Examples of such measurement of the hydrogen concentration in a member composed of titanium alloy, zirconium alloy, etc. using this principle are disclosed in the Japanese Patent Application Laid-open Publication No. 2001-141698 and the official gazette of Japanese Patent Application Publication No. 10-206934/1998.

Another known nondestructive method for hydrogen concentration measurement in the next place is a method by means of an ultrasonic method using a piezoelectric element.

For example, the Journal of Nuclear Material Vol. 252 (1998) discloses on pages 43 to 54 that by determining the longitudinal-wave sound speed of Zircaloy-2 with a plate thickness of 3 mm using a piezoelectric element exclusively for longitudinal-wave generation at around 10 MHz, and then determining the transverse-wave sound speed at the same location using an exchanged piezoelectric element exclusively for transverse-wave at around 2 MHz, the hydrogen concentration can be estimated from the ratio of the aforementioned sound speeds provided that a specific relation exists between the ratio of the sound speed of thus-obtained transverse wave to that of thus-obtained longitudinal wave and the hydrogen concentration.

As yet another nondestructive method for hydrogen concentration measurement, a method combining the phenomena of electromagnetic induction and ultrasonic resonance (an electromagnetic ultrasonic resonance method) has been proposed.

With regard to this method, the official gazette of the Japanese Patent Application No. 2000-375957 (the Japanese Patent Application Publication No. 2002-181795) and the Annual Meeting of the Atomic Energy Society of Japan (Spring 2001; Page L-44) disclose an instrument and a method for hydrogen concentration measurement wherein: a permanent magnet or electric magnet and a coil are placed on the surface of an object to be measured; the magnetic flux density in the proximity of the surface of the object is shifted by applying a high frequency wave to the coil by which elastic waves are generated directly on the surface of the object; two transverse ultrasonic waves are received, the vibrations of which deflecting in the directions parallel to the plane of the object and perpendicular to each other; the frequency of the coil is changed so that said two transverse ultrasonic waves form a resonant state; the resonance frequencies ($f_t$, $f_r$) of the two transverse ultrasonic waves are obtained; the relative difference $\Delta f$ (acoustic anisotropy) between $f_t$ and $f_r$ is calculated; and the hydrogen concentration in the object t is calculated making use of the relation:

$$\Delta f = (f_t - f_r)/f$$

provided that $f = (f_t + f_r)/2$ and H is provided as the hydrogen concentration of the object, $$H = a \cdot \Delta f + b$$

wherein a and b are coefficients. In addition, as a modification of the above method combining the phenomena of electromagnetic induction and ultrasonic resonance (an electromagnetic ultrasonic resonance method), the official gazette of the Japanese Patent Application No. 14-261406/2002 (the Japanese Patent Application Publication No. 2004-101281) proposes a nondestructive method for hydrogen concentration measurement wherein: the magnetic flux density with respect to an object to be measured is changed; using an electromagnetic ultrasonic sensor for receiving the ultrasonic wave generated in the object as a result of such change fixed at such an angle not to allow the long-axis direction of the coil of said electromagnetic ultrasonic sensor and the rolling direction of the object to overlap with each other, two different resonance frequencies corresponding to two kinds of elastic waves deflecting in the rolling direction of the object and the perpendicular direction relative to the aforementioned rolling direction, respectively, are obtained without rotating the electromagnetic ultrasonic sensor; and, based on this, the hydrogen concentration is calculated with high accuracy.

Since the electric conductivity, magnetic permeability, etc. to be measured are significantly affected by the gap between the sensor and the object to be measured in the above conventional nondestructive method for hydrogen concentration measurement making use of the electromagnetic properties, there are rather many technical problems to be solved such as in the calibration method for the distance of the gap between the sensor and the object to be measured.

Also the above conventional nondestructive method for hydrogen concentration measurement by means of the ultrasonic method using a piezoelectric element requires a coupling fluid for making close acoustic contact of the piezoelectric element with an object to be measured, polishing steps for obtaining a smooth surface, etc., thus making the labor complicated. In order to figure out the sound speed ratio of the longitudinal and transverse waves, this method requires either highly accurate measurement of the wall thickness of the object to be measured at the intended location or resonance frequency measurement with the two waves, longitudinal and transverse waves, at exactly the same location. However, such an object to be measured that industries are generally provided has a surface covered with scales, oxide films, contaminants, etc. and practically it is significantly difficult to determine the wall thickness with high accuracy by means of mechanical procedures. It is also difficult in general industrial situations to alternately contact the sensors, one exclusively for longitudinal waves and another exclusively for transverse waves, with exactly the same location. For these reasons, it has been difficult to yield correct results in the above conventional method using a piezoelectric element. Particularly, assuming application in high-temperature, radioactive or remote environment or to a narrow part of a heat exchanger tube etc. for example, on-site implementation of the sensor exchange is significantly difficult. In view of these facts, the aforementioned procedure using a piezoelectric element is difficult to apply in industry fields and limited to measuring procedures for laboratory studies. The above conventional nondestructive methods for hydrogen concentration measurement combining the phenomena of electromagnetic induction and ultrasonic resonance use the relation as described above: provided that two resonance frequencies of a first transverse ultrasonic wave whose vibration deflecting in the longitudinal (rolling) direction of an object to be measured and a second transverse ultrasonic wave deflecting in the direction at an angle of 90° with respect to said longitudinal direction (a lateral direction with respect to the rolling direction) are $f_r$ and $f_t$, respectively, and H is the hydrogen concentration of the object to be measured, $$H = a \cdot \Delta f + b$$

wherein a, b: coefficients $$\Delta f = (f_t - f_r)/f$$

$$\Delta f = (f_t + f_r)/2.$$

Study data demonstrated that, while the above coefficient a has a substantially constant value in the objects to be measured that are manufactured under the same member specifications (size, components, manufacturing method, etc.), the coefficient b varies within a significant range depending on the location within the object even if the members are manufactured under the same specifications.

That is, in obtaining the acoustic anisotropy Δf of an object to be measured, although a is a constant value by the member specifications, b is unknown because the value of b depends on the object and the location within the object, and thus the hydrogen concentration H cannot be identified.

In other words, if the change of Δf before and after hydrogen absorption in a certain object to be measured is obtained, it is possible to obtain the amount of the hydrogen concentration change by a·(change of Δt), but the absolute value of the hydrogen concentration cannot be calculated with b unknown.

Consequently, in the method proposed in the Japanese Patent Application No. 2000-375957 (the Japanese Patent Application Publication No. 2002-181795), the acoustic anisotropy Δf of a material whose hydrogen concentration is known needs to be figured out in order to obtain the absolute value (H) of hydrogen concentration from Δf. For example, Δf of an object to be measured without hydrogen added (initial state) needs to be measured.

That is to say, the method proposed in the Japanese Patent Application No. 2000-375957 (the Japanese Patent Application Publication No. 2002-181795) has a limit that its application is restricted to a so-called fixed-point observational measurement wherein the acoustic anisotropy is measured at each specific location at the manufacturing stage in advance and then the absolute value of hydrogen concentration is determined by repeating the measurement of the same location.

However, such a nondestructive method for hydrogen concentration measurement that can be applied only to a measurement in a manner of fixed-point observation is inconvenient without being capable of measuring the hydrogen concentration of any given region of an object to be measured. In this connection, the present invention provides the art of obtaining the hydrogen concentration of any given location of an object to be measured at the time of measurement by eliminating the need for the value measured in the state of no hydrogen content to obtain the absolute value of hydrogen concentration, unlike the conventional nondestructive methods for hydrogen concentration measurement by means of the electromagnetic ultrasonic resonance method, to solve the problems.

SUMMARY OF THE INVENTION

The present inventors accumulated their dedication to the study on the relation between hydrogen concentration of various materials and the acoustic property measured using the electromagnetic ultrasonic resonance method, searching for an acoustic property index in which the conflicting properties, insensitive to the differences of the manufacturing lot and measurement location of an object to be measured and at the same time sensitive to the contrary to an increase of hydrogen concentration, are combined, and have achieved the present invention.

In the method for measuring hydrogen concentration of a member comprising the steps of: placing an electromagnetic ultrasonic sensor in the proximity of, or on, the surface of an object to be measured; applying a changing magnetic field to the object to be measured by said electromagnetic ultrasonic sensor; and receiving an ultrasonic wave generated in the object to be measured by said changing magnetic field, the method for measuring hydrogen concentration in a member according to the present invention is characterized by comprising the steps of: receiving a longitudinal ultrasonic wave vibrating in the thickness direction of the object to be measured; adjusting the frequency of the changing magnetic field so that said longitudinal ultrasonic wave is caused to resonate; receiving a transverse ultrasonic wave vibrating in the direction parallel to the surface of the object to be measured; adjusting the frequency of the changing magnetic field so that said transverse ultrasonic wave is caused to resonate; detecting a resonance frequency of each of said longitudinal ultrasonic wave and said transverse ultrasonic wave; calculating a resonance property index from the detected resonance frequency of the longitudinal ultrasonic wave and the detected resonance frequency of the transverse ultrasonic wave; and calculating the hydrogen concentration of the object to be measured by comparing the calculated resonance property index and a reference material data storing the relation between the hydrogen concentration in a member of the same specifications as the object to be measured and said resonance property index.

Said transverse ultrasonic wave may include at least either one of a first transverse ultrasonic wave vibrating in the rolling direction of the object to be measured and a second transverse ultrasonic wave vibrating in the lateral direction with respect to said rolling direction; and said resonance property index may be provided by a dimensionless function including $f_l$ and at least either one of $f_r$ and $f_t$, wherein $f_l$ is the resonance frequency of said longitudinal ultrasonic wave, $f_r$ is the resonance frequency of said first transverse ultrasonic wave and $f_t$ is the resonance frequency of said second transverse ultrasonic wave.

The instrument for measuring hydrogen concentration of a member according to the present invention is characterized by comprising: an electromagnetic ultrasonic sensor which is placed in the proximity of, or on, the surface of an object to be measured, applies a changing magnetic field to the object to be measured and receives an ultrasonic wave generated in the object to be measured by said changing magnetic field; an electromagnetic ultrasonic wave transmitter/receiver which outputs a voltage of a predetermined frequency for generating an electromagnetic wave to said electromagnetic ultrasonic sensor and inputs an electric signal of the ultrasonic wave received by said electromagnetic sensor; a control/record means which controls the frequency of the voltage output by said electromagnetic ultrasonic wave transmitter/receiver so that the ultrasonic wave generated in said object to be measured is caused to resonate and records the frequency and amplitude of the ultrasonic wave input by said electromagnetic ultrasonic wave transmitter/receiver; a resonance property index calculation means which calculates a resonance property index of the object to be measured from the frequency and amplitude of the ultrasonic wave recorded by said control/record means; a reference material database storing the relation between the hydrogen concentration and the resonance property index of a member; and a hydrogen concentration output means which obtains, from said reference material database, and outputs the hydrogen concentration corresponding to the calculated resonance property index, wherein said resonance property index calculation means calculates the resonance property index from the frequency of a longitudinal ultrasonic wave vibrating in the thickness direction of the object to be measured and the frequency of a transverse ultrasonic wave vibrating in the direction parallel to the surface of the object to be measured.

Said transverse ultrasonic wave may include at least either one of a first transverse ultrasonic wave vibrating in the rolling direction of the object to be measured and a second transverse ultrasonic wave vibrating in the lateral direction with respect to said rolling direction; and said resonance property index calculation means may calculate the resonance property index provided by a dimensionless function including $f_l$ and at least either one of $f_r$ and $f_t$, wherein $f_l$ is the resonance frequency of said longitudinal ultrasonic wave, $f_r$ is the resonance frequency of said first transverse ultrasonic wave and $f_t$ is the resonance frequency of said second transverse ultrasonic wave.

Whereas in the conventional art the hydrogen concentration is measured using only the resonance frequency of a transverse ultrasonic wave whose vibration deflecting in the direction parallel to the plane of the wall body of an object to be measured, in the method and instrument for the measurement according to the present invention, the resonance frequency of a longitudinal ultrasonic wave whose vibration deflecting in the direction parallel to the thickness direction of the wall body of an object to be measured is newly introduced, and the hydrogen concentration is measured by means of the corresponding relation between a specific index (resonance property index) calculated from the resonance frequencies of the longitudinal and transverse ultrasonic waves and the hydrogen concentration.

Experiments have revealed that the above index (resonance property index) is insensitive to the differences of the manufacturing lot and the measurement location on one side and sensitive to the change of the hydrogen concentration on the other side. That is to say, the initial value of the above resonance property index of a member manufactured under certain member specifications is substantially the same as the resonance property index of other members manufactured under the same member specifications. In addition, the above resonance property indexes are also substantially the same at different measurement locations as long as the members with the same member specifications have the same hydrogen concentration.

By means of the property of the above resonance property index, the present invention enables the measurement of the magnitude of hydrogen concentration of an object to be measured that has no data on the initial state. In addition, the magnitude of hydrogen concentration of an object can be measured regardless of the measurement location.

That is, according to the present invention, the value of hydrogen concentration of an object to be measured with different manufacturing lot, which is not possible to be obtained in the conventional art, can be directly obtained at any given location with high accuracy without acoustic property data in the initial manufacturing process.

BEST EMBODIMENTS FOR REALIZING THE INVENTION

The embodiments of the present invention will be explained hereinafter with reference to the accompanying drawings.

Figure 1:
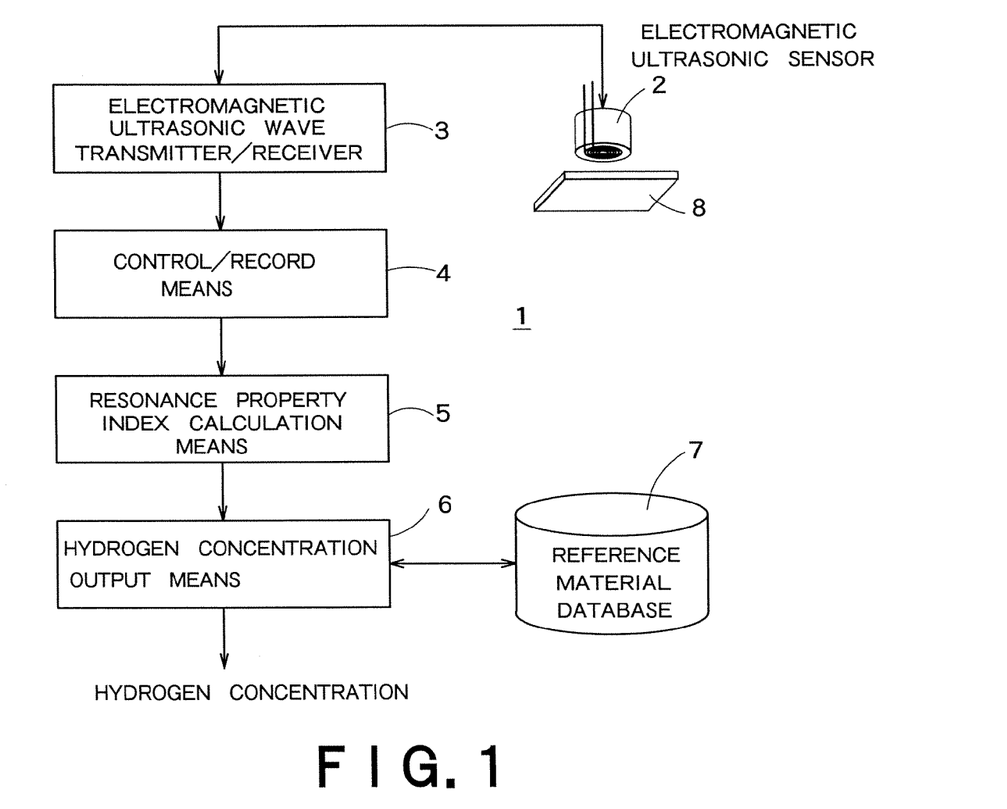
FIG. 1 is a block diagram showing the constitution and the process flow of a hydrogen concentration measuring instrument according to an embodiment of the present invention.

FIG. 1 shows the constitution of a hydrogen concentration measuring instrument 1 according to an embodiment of the present invention and the process flow across the constituents.

The hydrogen concentration measuring instrument 1 has an electromagnetic ultrasonic sensor 2, an electromagnetic ultrasonic wave transmitter/receiver 3, a control/record means 4, a resonance property index calculation means 5, a hydrogen concentration output means 6, and a reference material database 7. The reference numeral 8 represents an object to be measured. The object to be measured 8 may be a flat-plate-shaped member or a part of a member which is tubular, spherical, etc.

The electromagnetic ultrasonic sensor 2 has a function to generate a magnetic field in which the magnetic flux density changes at high frequency on the wall body of the object to be measured 8 and receive simultaneously a longitudinal ultrasonic wave and a transverse ultrasonic wave generated in the object to be measured 8 due to the changing magnetic field, the vibration of said longitudinal ultrasonic wave deflecting in the direction parallel to the thickness direction of the object to be measured 8, the vibration of said transverse ultrasonic wave deflecting in the direction at an angle of substantially 90° with respect to the above longitudinal direction.

The measurement of the hydrogen concentration in the object to be measured 8 by means of the hydrogen concentration measuring instrument 1 is performed as follows.

The electromagnetic ultrasonic sensor 2 is placed on or in the proximity of the surface of the wall body of the object to be measured 8.

Then the process of transmitting/receiving the changing magnetic field and the ultrasonic waves is performed. Firstly, the control/record means 4 outputs the control signal for the output voltage frequency of the electromagnetic ultrasonic wave transmitter/receiver 3 to the electromagnetic ultrasonic wave transmitter/receiver 3 so that a resonant state of the above longitudinal and transverse ultrasonic waves is formed in the object to be measured 8. This control signal allows the electromagnetic ultrasonic wave transmitter/receiver 3 to output a changing voltage to the electromagnetic ultrasonic sensor 2 which then generates a magnetic field in which the magnetic flux density changes at high frequency. Due to the magnetic flux density change in the proximity of the object to be measured 8 at high frequency, the above longitudinal and transverse ultrasonic waves are generated in the object to be measured 8. The electromagnetic ultrasonic sensor 2 receives and outputs to the electromagnetic ultrasonic wave transmitter/receiver 3 the longitudinal and transverse ultrasonic waves generated in the object to be measured 8. The electromagnetic ultrasonic wave transmitter/receiver 3 transmits the received signals of the longitudinal and transverse ultrasonic waves to the control/record means 4, and the control/record means 4 records said signals of the longitudinal and transverse ultrasonic waves.

Then, from the control/record means 4, the signals of the longitudinal and transverse ultrasonic waves received by the electromagnetic ultrasonic sensor 2 are input to the resonance property index calculation means 5 which then detects the resonance frequency of the longitudinal wave and that of the transverse ultrasonic wave, and calculates a resonance property index using the above resonance frequencies of the longitudinal and transverse ultrasonic waves. The present inventors have found that said resonance property index has correlation with the hydrogen concentration of the object to be measured 8. A detailed explanation of the resonance property index follows later. Then, from the resonance property index calculation means 5, the above resonance property index is input to the hydrogen concentration output means 6 which then makes reference to the reference material database 7. The reference material database 7 stores the resonance property index and the hydrogen concentration of a member of the same member specifications as the object to be measured 8, corresponding to each other. The hydrogen concentration output means 6 searches for the resonance property index and the corresponding hydrogen concentration stored in the reference material database 7 and outputs said hydrogen concentration.

Note that a member of the same member specifications indicates that the member specifications of a member such as size, components, manufacturing method, etc. are the same. Even if the manufacturing lot, the region of the member, etc. are different, the member can be considered to be a member of the same member specifications as long as the member specifications are the same.

Figure 2:
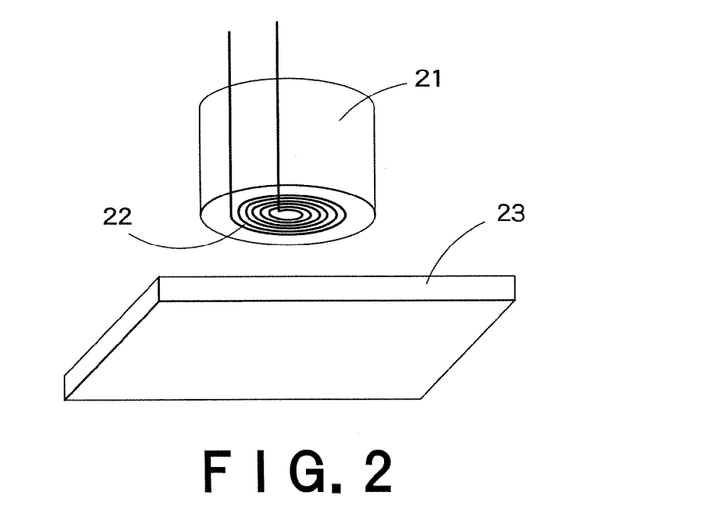
FIG. 2 is a perspective view showing an example of an electromagnetic ultrasonic sensor.

FIG. 2 is a public domain example of an electromagnetic ultrasonic sensor, called EMAT in the electromagnetic ultrasonic resonance method, having a configuration in which a high frequency transmitting coil 22 is placed at one end of an permanent magnet 21, the both ends of which being magnetized to have a S pole and an N pole, respectively, and receiving coils of the same shape, not shown, are mounted one above another, and a function that can transmit/receive the longitudinal and transverse ultrasonic waves simultaneously. The reference numeral 23 represents an object to be measured.

Figure 3:
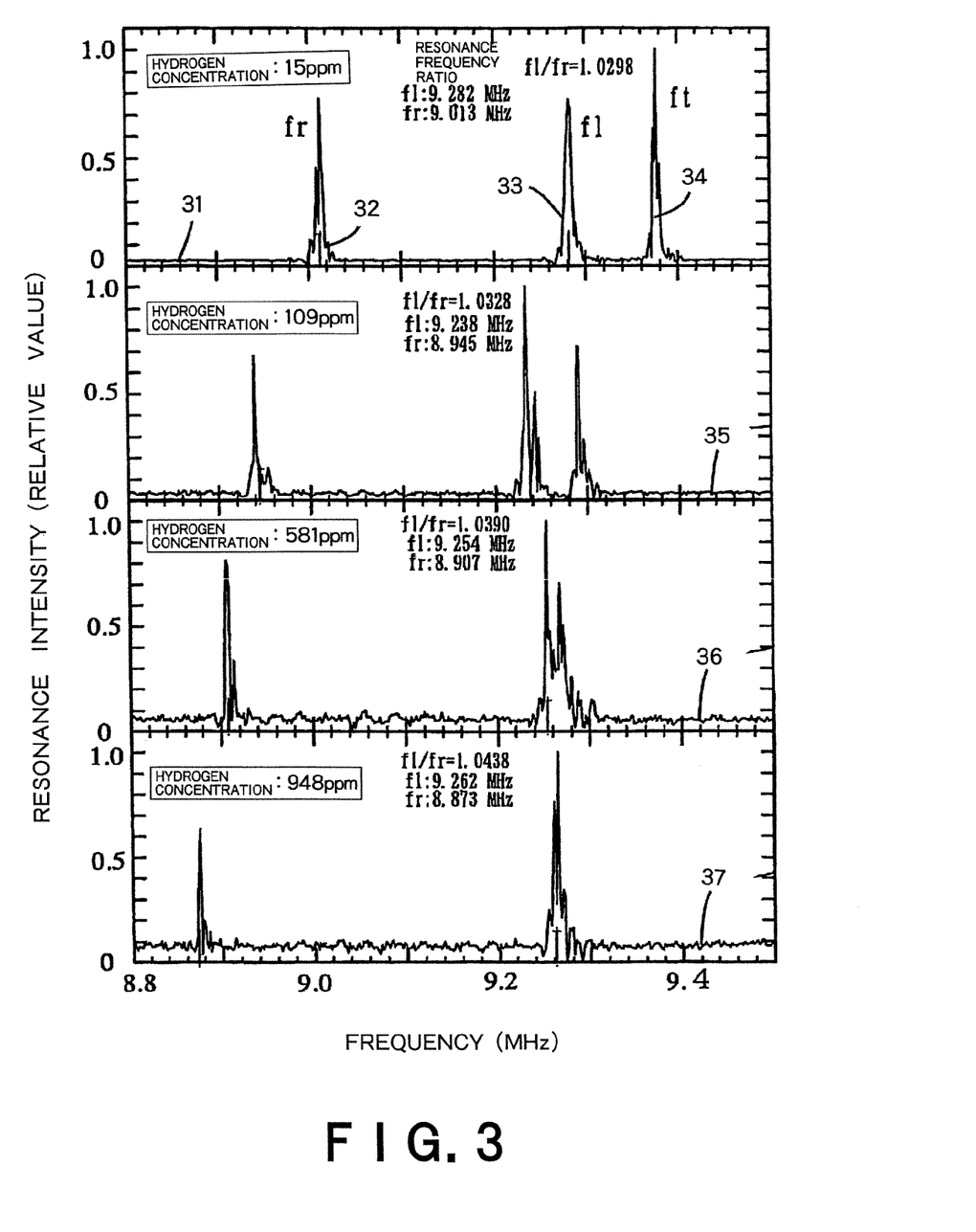
FIG. 3 is a graph showing the relation between hydrogen concentration and the resonance spectra of longitudinal waves and transverse waves.

FIG. 3 shows a resonance spectrum 31 of a thin plate at the manufacturing stage before hydrogen absorption showing that this resonance spectrum 31 has a resonance frequency $f_r$ (32) of the transverse ultrasonic wave whose vibration is deflecting in the longitudinal (rolling) direction of the object to be measured, a resonance frequency $f_t$ (34) of the transverse ultrasonic wave deflecting in the direction at an angle of 90° with respect to the longitudinal direction, and a resonance frequency $f_l$ (33) of the longitudinal ultrasonic wave whose vibration direction is the plate-thickness direction of the object to be measured.

In particular, the above resonance spectrum was measured as follows.

A band plate material for constructing a component of a nuclear fuel assembly, called a spacer, is manufactured in such a way that a zirconium alloy slab, called Zircaloy, is rolled into a thin and lengthy plate with 0.5-mm thickness and then cut to a prescribed length.

With the surface of such plate material manufactured in this way, presented as the object to be measured 8, the coil 22 of the electromagnetic ultrasonic sensor 2 shown in FIG. 2 was contacted.

Having the electromagnetic ultrasonic sensor 2 wire-connected to the electromagnetic ultrasonic wave transmitter/receiver 3, the control/record means 4 makes short-time transmission of a high frequency wave of a predetermined fixed frequency in a burst manner and receives the response signal corresponding to the predetermined frequency. As a result of gradually increasing the predetermined frequency for the short-time transmission from 8.8 MHz to 9.5 MHz, the resonance spectrum 31 and, under the conditions satisfying the resonance conditions, the above described three resonance frequencies, $f_r$ (32), $f_t$ (34) and $f_l$ (33) were obtained. By corroding the aforementioned material in high-temperature steam, samples with hydrogen concentration of 109 ppm, 581 ppm and 948 ppm, measured destructively, were prepared, and the resonance spectra and resonance frequencies shown as the reference numerals 35, 36 and 37 in FIG. 3 were obtained.

The inventors carried out the same hydrogen addition procedure on 6 kinds, A, B, C, E, F and G, of a band plate material for constructing a component of a nuclear fuel assembly, called a spacer, manufactured under the same specifications but in different lots, and dedicated themselves to the study on the correlation between each resonance frequency and hydrogen concentration in the object to be measured for such an index that was hardly affected by the difference of the lot.

Figure 4:
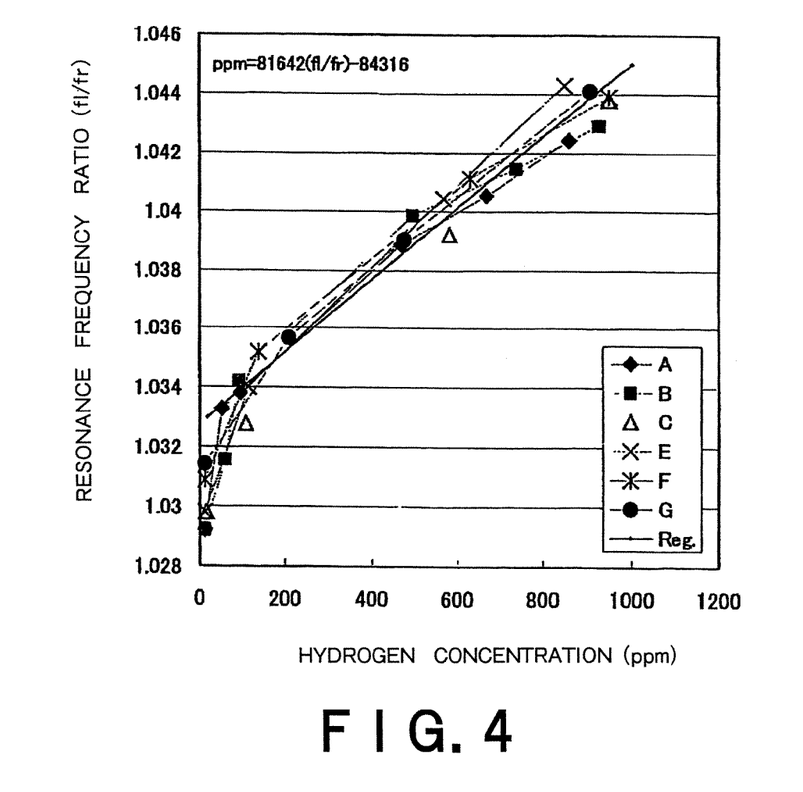
FIG. 4 is a graph showing the relation between the resonance frequency ratio and hydrogen concentration.

The newly found fact as a result was that, provided that $(f_l/f_r)$ (hereinafter referred to as a resonance frequency ratio) was an index as an ultrasonic property, the relation between $f_l/f_r$ and the hydrogen concentration was hardly affected by the difference of the lot, as shown in FIG. 4.

In the calculation processing for the resonance property index by means of the resonance property index calculation means 5, the resonance frequency $f_l$ of the longitudinal ultrasonic wave is divided by the resonance frequency $f_r$, the lower of the resonance frequencies of the transverse ultrasonic waves, hydrogen is added to the reference material (plate material) manufactured under the same member specifications to provide several levels, the relations of those resonance frequency ratios and the hydrogen concentrations are stored in the reference material database 7, and using the calculated resonance frequency ratio $(f_l/f_r)$ the hydrogen concentration can be calculated from the corresponding relation between the resonance frequency ratio $(f_l/f_r)$ and the hydrogen concentration in the reference material database 7.

Although the resonance frequency ratio $(f_l/f_r)$ is used as an embodiment of the resonance property index as shown in FIG. 4, the resonance property index is not limited to the exemplified function as a matter of course and may be any dimensionless function having the denominator and numerator of the same order and including at least one of the resonance frequencies of the longitudinal ultrasonic wave and the two transverse ultrasonic waves. The resonance property index given by such function is hardly affected by the difference of the manufacturing lot of the member and has a direct correlation with the hydrogen concentration as well. In addition to $f_l/f_r$, such resonance property index may include, for example, $f_l/f_t$, $f_l/(f_r+f_t)$, $(f_r^2+f_t^2)/(f_r^2+f_t^2+f_l^2)$, etc. or any combination thereof formulated in dimensionless form. It is obvious that these indexes are included in the gist of the present invention because a certain correlation is observed between the hydrogen concentration and the resonance property index regardless of the difference of the manufacturing lot.

In connection with the resonance spectrum 31 in FIG. 3, $f_r$ [the resonance frequency of the transverse ultrasonic wave whose vibration is deflecting in the longitudinal (rolling) direction of the object to be measured], $f_l$ (the resonance frequency of the longitudinal ultrasonic wave whose vibration direction is the plate-thickness direction) and $f_t$ [the resonance frequency of the transverse ultrasonic wave deflecting in the direction at an angle of 90° with respect to the longitudinal direction (a lateral direction with respect to the rolling direction)] are provided in ascending order of the resonance frequency, which will be specifically justified on a theoretical basis. The resonance frequencies $f_r$, $f_t$, $f_l$, the transmission phenomena of ultrasonic waves in solid materials, can be expressed in terms of solutions to the wave equations as:

$$f_r = n \cdot (C_{55}/p)^{0.5}/(2t)$$

$$f_t = n \cdot (C_{66}/p)^{0.5}/(2t)$$

$$f_l = n \cdot (C_{11}/p)^{0.5}/(2t),$$

provided that n is the degree of the resonance, t is the plate thickness, p is the material density, and $C_{11}$, $C_{55}$ and $C_{66}$ are the elasticity constants of the zirconium alloy, respectively.

In this case, $C_{55}$ is the elasticity constant of the shear strain and stress in the longitudinal (rolling) direction of the object to be measured, $C_{66}$ is the elasticity constant of the shear strain and stress in the direction at an angle of 90° with respect to the longitudinal direction (a lateral direction with respect to the rolling direction) and $C_{11}$ is the elasticity constant of the strain and stress in the plate-thickness direction. The elastic property $C_{11}$, $C_{55}$ and $C_{66}$ of the thin plate made of Zircaloy at 20° C. were calculated in consideration of the texture of the plate as approximately 149 GPa, 34.3 GPa and 36.9 GPa, respectively, and thereby:

$$f_r = n \cdot 5.857(1/p)^{0.5}/(2t)$$

$$f_t = n \cdot 6.075(1/p)^{0.5}/(2t)$$

$$f_l = n \cdot 12.21(1/p)^{0.5}/(2t).$$

Generally it is known that the resonance frequency derived theoretically from the elastic property of a material comes close to the approximate value although such value, strictly speaking, does not coincide with the calculated value using a measured value and the elastic property, as the accuracy of the resonance frequency is not as high as that obtained by the ultrasonic method. From the viewpoint of the numerical values derived from the elastic property, $f_r < f_t < f_l$, and in a homogeneous comparison, the resonance frequency $f_l$ of the longitudinal transverse wave is about double those of the transverse ultrasonic waves, and from the viewpoint of the same frequency range, on the other hand, the secondary resonance frequency of the longitudinal ultrasonic wave appears in the proximity of the quaternary resonance frequencies of the transverse ultrasonic waves for example. With such corresponding relation, for example, the resonance frequencies of the transverse ultrasonic waves are identified due to the fact that the resonance of the longitudinal ultrasonic wave does not appear in the proximity of the resonance frequencies of the transverse ultrasonic waves in the tertiary resonance, and by multiplying the identified resonance frequency by 4/3, the quaternary resonance frequencies of the transverse ultrasonic waves can be identified, and thus the remaining peak in the resonance spectrum can be identified as the secondary resonance frequency of the longitudinal ultrasonic wave. In this way the location of the resonance frequencies of the longitudinal wave and the two transverse waves can be identified in the resonance spectrum. Additionally, from the viewpoint of the aforementioned function form with the $f_r$, $f_t$ and $f_l$, the material density p and the plate thickness t, the function comprising homogeneous fractions applied as the index results in values of nondimensional numbers without the density and the plate thickness, and the index can thus be considered not to be essentially affected by material density and plate thickness.

Figure 5:
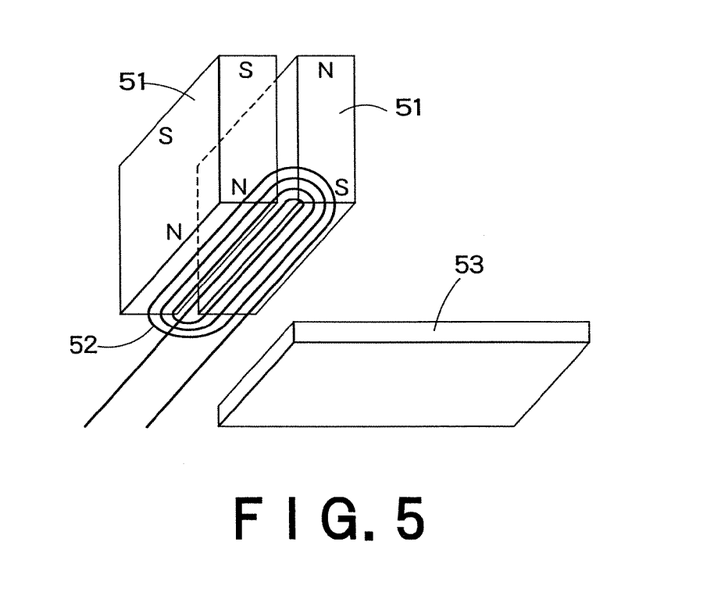
FIG. 5 is a perspective view showing an example of an electromagnetic ultrasonic sensor.

Other than the sensor for electromagnetic ultrasonic resonance in FIG. 2 shown in this embodiment, the equivalent resonance spectrum can be obtained with an electromagnetic ultrasonic sensor in which a coil is placed in a track shape on S and N poles, as shown in FIG. 5.

That is, the equivalent resonance property to that in FIG. 2 can be obtained by bringing an electromagnetic ultrasonic sensor close to an object to be measured 53, said sensor having two permanent magnets 51 and a coil 52 placed such a way that the longitudinal direction of the end surface on each magnet and the linear portion of the coil 52 are parallel and the magnetic poles are opposite to each other.

In this embodiment, an example for the measurement of a flat plate made of zirconium alloy has been shown, but any electrically conducting material producing hydride, preferably a rolling material whose principal component is hexagonal crystal such as titanium, zirconium, etc., is applicable as the object to be measured. The form is not limited to a flat plate, and a spherical container, a cylindrical structure, etc. are also applicable. With the electromagnetic ultrasonic sensors shown in FIGS. 6 and 7, the nondestructive measurement of hydrogen concentration can be performed from the inside of a heat exchanging tube made of titanium alloy often used in oil refining industry etc., for example.

Figure 6:
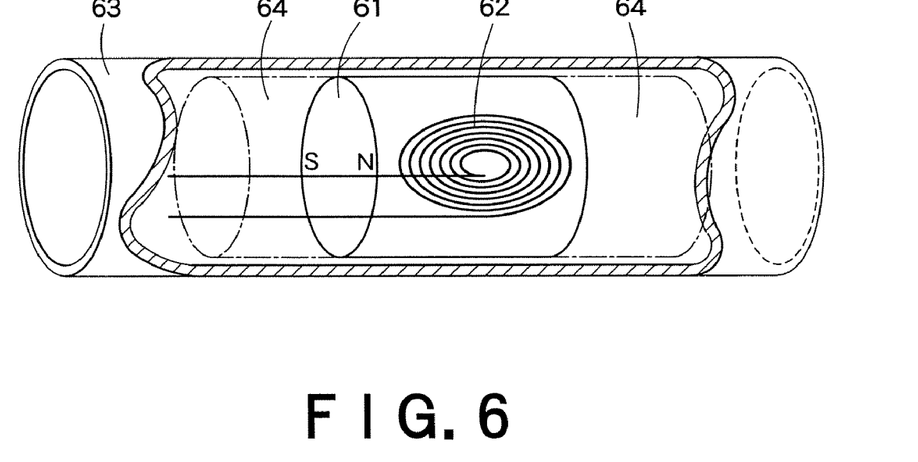
FIG. 6 is a perspective view showing an example of an electromagnetic ultrasonic sensor.

In this case in FIG. 6, a bar permanent magnet 61 which is magnetized to have a S pole and an N pole at both ends of its diameter, respectively, is placed, and a spiral coil 62 is placed on one of the poles (e.g. N pole). The electromagnetic ultrasonic sensor is furnished with a guide 64 made of non-magnetic substance at both ends of the magnet in order to maintain stability of the magnet during transportation and can detect the ultrasonic property at each location by insertion in a tube presented as an object to be measured 63.

Figure 7:
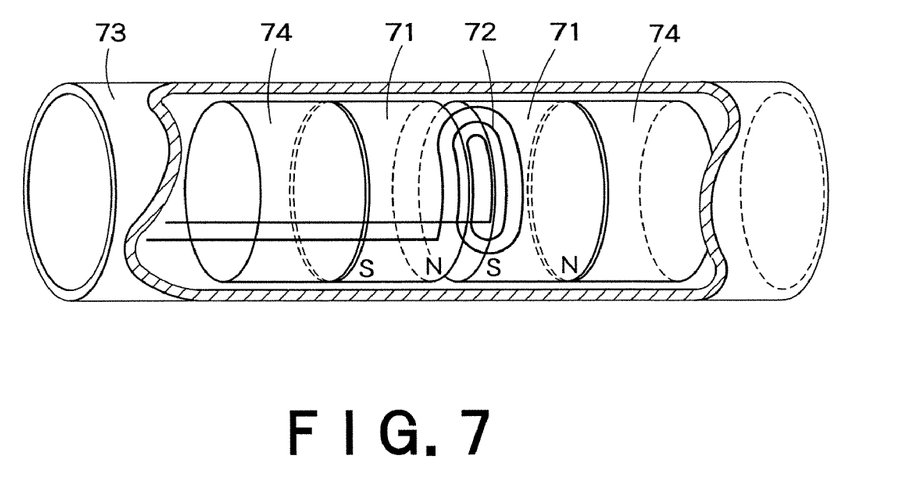
FIG. 7 is a perspective view showing an example of an electromagnetic ultrasonic sensor.

The above electromagnetic ultrasonic sensor for the measurement by insertion in the tube is not limited to the one in FIG. 6, and FIG. 7 shows an electromagnetic ultrasonic sensor in which a track-shaped coil 72 is placed on the outer surface of two permanent magnets 71 provided as bar magnets magnetized at both ends in the longitudinal direction, and on both sides, guides 74 made of non-magnetic substance for relocation are provided. By insertion in a tube 73 as an object to be measured in the same manner as in FIG. 6, the equivalent measurement can be carried out.

Although FIGS. 6 and 7 show the examples of the measurement by insertion in an object to be measured, note that it is obvious as a matter of course that the measurement can also be carried out by placing the electromagnetic ultrasonic sensor outside the object to be measured. The advantages obtained by the present invention will be explained in contrast to the measurement results obtained by the conventional art for determining hydrogen concentration by means of the relation of the resonance frequencies of two transverse ultrasonic waves (hereinafter referred to as the "conventional art making use of transverse waves").

Figure 8:
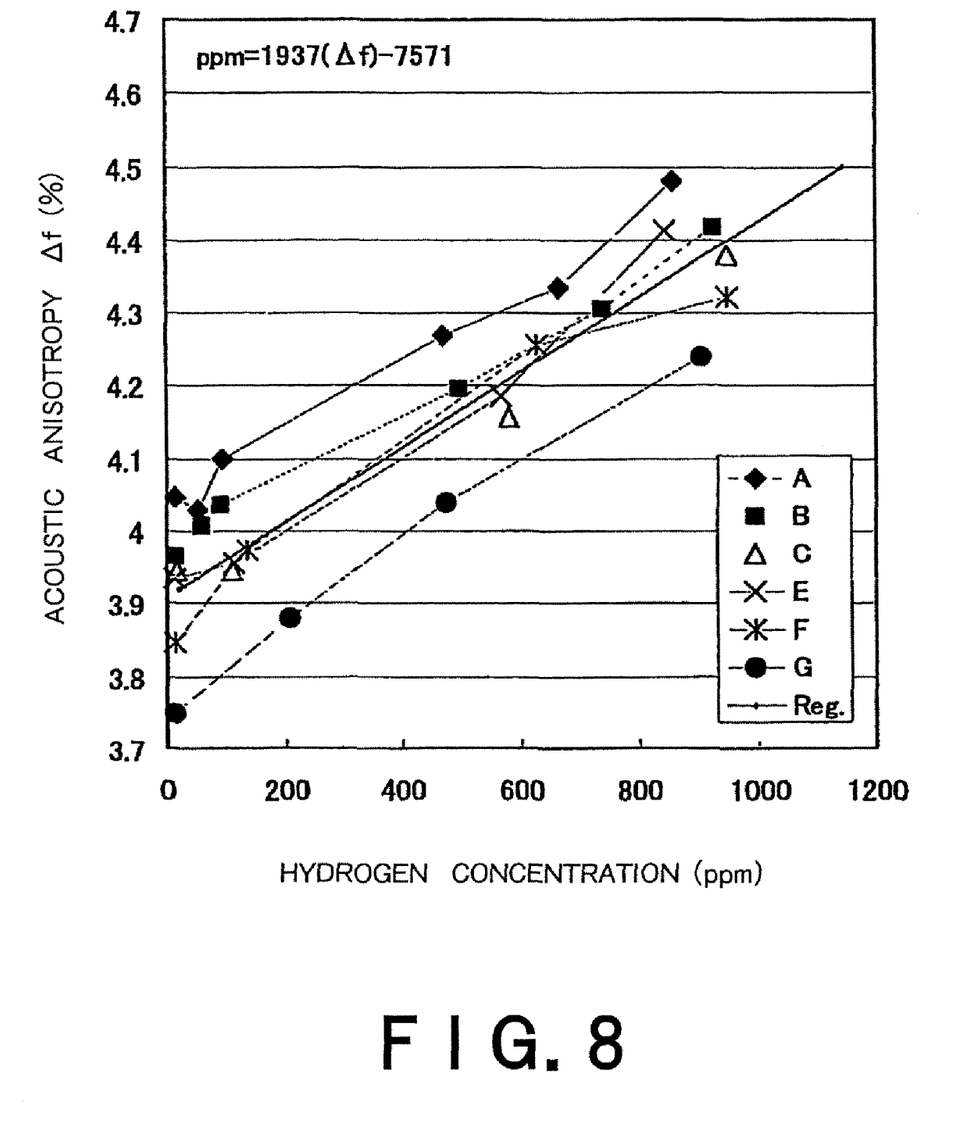
FIG. 8 is a graph showing the relation between the index according to the conventional art which makes use only of a resonance frequency of transverse ultrasonic waves and hydrogen concentration.

FIG. 8 shows the measurement results obtained by the conventional art making use of transverse waves.

For the measurement by the conventional art making use of transverse waves, objects to be measured were prepared by adding hydrogen to spacer band plate materials for a nuclear fuel assembly, having the same member specifications but in different manufacturing lots, A, B, C, E, F, G, to provide each concentration level. The acoustic anisotropy $\Delta f$ was determined for the materials prepared in this way by the conventional measurement method making use of transverse waves, and the relation between the obtained $\Delta f$ and the hydrogen concentration is as shown in FIG. 8.

The acoustic anisotropy $\Delta f$ of the conventional art making use of transverse waves is substantially affected by the difference of the lot even though the plate materials are manufactured under the same member specifications, wherein the error in the same $\Delta f$ is 500 ppm at a maximum (mean value: ±250 ppm), and the relation of the acoustic anisotropy ($\Delta f$) and the hydrogen concentration is not specified even if the manufacturing specifications are the same, thus proving the difficulty of the hydrogen concentration determination from the acoustic anisotropy $\Delta f$.

From the viewpoint of application, the conventional art making use of transverse waves is restricted to a measurement in a manner of fixed-point observation wherein the acoustic anisotropy $\Delta f_0$ is measured at each location to be measured at the manufacturing stage before hydrogen absorption in advance, and the acoustic anisotropy $\Delta f$ is measured after hydrogen absorption, and then ($\Delta f - \Delta f_0$) is multiplied by a coefficient for conversion to hydrogen concentration.

On the contrary, in the measurement method according to the present invention (the measuring method making use of longitudinal waves), by arrangement based on the relation (as shown in the preceding FIG. 4) between the resonance frequency ratio ($f_l/f_r$) and the hydrogen concentration, the difference of the lot has significantly less affect, and the variation of the hydrogen concentration of the 6 kinds of the lot at the same resonance frequency ratio ($f_l/f_r$) is proved that the range is within 100 ppm at a maximum (mean value: ±50 ppm) at 1000 ppm (refer to FIG. 4).

In comparison between FIG. 4 and FIG. 8, while the error is large in the conventional measurement method making use only of the transverse ultrasonic waves if the manufacturing lot is different regardless of manufacturing under the same member specifications and ultrasonic property data at the manufacturing stage are required, in the measurement method using a longitudinal ultrasonic wave according to the present invention, the advantage of improvement is significant wherein the magnitude of hydrogen concentration can be calculated directly from the resonance frequency ratio ($f_l/f_r$) for any other manufacturing lots by determining the relation between the hydrogen concentration and the resonance frequency ratio ($f_l/f_r$) in advance as long as the member is manufactured under specific member specifications. Described next is the difference between the present invention making use of longitudinal and transverse ultrasonic waves and the preceding conventional art making use of piezoelectric elements and likewise of longitudinal and transverse ultrasonic waves (hereinafter referred to as the "conventional art making use of piezoelectric elements").

The art according to the present invention is essentially different from the conventional art making use of piezoelectric elements in terms of the following issues.

Firstly, the conventional art making use of piezoelectric elements requires detection/measurement of the plate thickness of an object to be measured with significantly high accuracy in order to determine the sound speed with high accuracy. On the contrary, the art according to the present invention requires no plate-thickness data of the measurement location.

Secondly, in the conventional art using piezoelectric elements, the resonance frequency is provided by the resonance of the whole vibration system of a sensor including a piezoelectric element, a casing, etc. and an object to be measured. Consequently, the errors caused by the vibration of the whole system including the sensor are inevitable, in contrast to the resonance property determination solely of the material as in the electromagnetic ultrasonic resonance method of the present invention.

Thirdly, the conventional art making use of piezoelectric elements generally requires use of sensors for exclusive use, i.e. a sensor for longitudinal waves and another for transverse waves. However, placing 2 kinds of elements at the same point of the location of the measurement inevitably leads to reduced accuracy. On the contrary, in the art according to the present invention, longitudinal and transverse ultrasonic waves can be received at one measurement location, thus not leading to reduced measurement accuracy.

Fourthly, the electromagnetic ultrasonic sensor of the present invention is furnished in the compact sensor body with a function that can transmit/receive longitudinal and transverse waves simultaneously, and a remote measurement can be carried out in a narrow part such as in a tube with a small diameter. On the contrary, in the conventional art making use of piezoelectric elements, the same location is measured with 2 kinds of sensors (a sensor for longitudinal waves and another for transverse waves) exchanged one for the other, involving significant difficulty in the environment of industrial equipment fields. According to the art of the present invention, the result of use under a severe field environment shows that two acoustic properties of longitudinal/transverse waves can be detected only through a single placement of the sensor even if the object to be measured has scales, oxide films, contaminants, etc. deposited on the surface, and also the hydrogen concentration is predictable with high accuracy.

The invention claimed is:

1. A method for measuring hydrogen concentration in a member comprising the steps of:
   placing an electromagnetic ultrasonic sensor in the proximity of, or on, the surface of an object to be measured;
   applying a changing magnetic field to the object to be measured by said electromagnetic ultrasonic sensor; and
   receiving an ultrasonic wave generated in the object to be measured by said changing magnetic field,
   the method characterized by comprising the steps of:
   receiving a longitudinal ultrasonic wave vibrating in the thickness direction of the object to be measured;
   adjusting the frequency of the changing magnetic field so that said longitudinal ultrasonic wave is caused to resonate;
   receiving a transverse ultrasonic wave vibrating in the direction parallel to the surface of the object to be measured;
   adjusting the frequency of the changing magnetic field so that said transverse ultrasonic wave is caused to resonate;
   detecting a resonance frequency of each of said longitudinal ultrasonic wave and said transverse ultrasonic wave;
   calculating a resonance property index from the detected resonance frequency of the longitudinal ultrasonic wave and the detected resonance frequency of the transverse ultrasonic wave; and
   calculating the hydrogen concentration of the object to be measured by comparing the calculated resonance property index and a reference material data storing the relation between the hydrogen concentration in a member of the same specifications as the object to be measured and said resonance property index.

2. A method for measuring hydrogen concentration in a member according to claim 1, characterized in that:
   said transverse ultrasonic wave includes at least either one of a first transverse ultrasonic wave vibrating in a rolling direction of the object to be measured and a second transverse ultrasonic wave vibrating in the lateral direction with respect to said rolling direction; and
   said resonance property index is provided by a dimensionless function including $f_l$ and at least either one of $f_r$ and $f_t$, wherein $f_l$ is the resonance frequency of said longitudinal ultrasonic wave, $f_r$ is the resonance frequency of said first transverse ultrasonic wave and $f_t$ is the resonance frequency of said second transverse ultrasonic wave.

3. An instrument for measuring hydrogen concentration of a member characterized by comprising:
   an electromagnetic ultrasonic sensor which is placed in the proximity of, or on, the surface of an object to be measured, applies a changing magnetic field to the object to be measured and receives an ultrasonic wave generated in the object to be measured by said changing magnetic field;
   an electromagnetic ultrasonic wave transmitter/receiver which outputs a voltage of a predetermined frequency for generating an electromagnetic wave to said electromagnetic ultrasonic sensor and inputs an electric signal of the ultrasonic wave received by said electromagnetic ultrasonic sensor;
   a control/record means which controls the frequency of the voltage output by said electromagnetic ultrasonic wave transmitter/receiver so that the ultrasonic wave generated in said object to be measured is caused to resonate and records the frequency and amplitude of the ultrasonic wave input by said electromagnetic ultrasonic wave transmitter/receiver;
   a resonance property index calculation means which calculates a resonance property index of the object to be measured from the frequency and amplitude of the ultrasonic wave recorded by said control/record means;
   a reference material database storing the relation between the hydrogen concentration and the resonance property index of a member; and
   a hydrogen concentration output means which obtains, from said reference material database, and outputs the hydrogen concentration corresponding to the calculated resonance property index,
   wherein said resonance property index calculation means calculates the resonance property index from the resonance frequency of a longitudinal ultrasonic wave vibrating in the thickness direction of the object to be measured and the resonance frequency of a transverse ultrasonic wave vibrating in the direction parallel to the surface of the object to be measured.

4. An instrument for measuring hydrogen concentration of a member according to claim 3, characterized in that:
   said transverse ultrasonic wave includes at least either one of a first transverse ultrasonic wave vibrating in a rolling direction of the object to be measured and a second transverse ultrasonic wave vibrating in the lateral direction with respect to said rolling direction; and
   said resonance property index calculation means calculates the resonance property index provided by a dimensionless function including $f_l$ and at least either one of $f_r$ and $f_t$, wherein $f_l$ is the resonance frequency of said longitudinal ultrasonic wave, $f_r$ is the resonance frequency of said first transverse ultrasonic wave and $f_t$ is the resonance frequency of said second transverse ultrasonic wave.

* * * * *